(12) United States Patent
Othman et al.

(10) Patent No.: US 6,970,738 B1
(45) Date of Patent: Nov. 29, 2005

(54) COMPLEX IMPEDANCE SPECTROMETER USING PARALLEL DEMODULATION AND DIGITAL CONVERSION

(75) Inventors: Salah Othman, Coyoacán (MX); Emilio Sacristán Rock, Tlalpan (MX)

(73) Assignee: Innovamedica S.A. de C.V., Tlalpan (MX)

( * ) Notice: Subject to any disclaimer, the term of this patent is extended or adjusted under 35 U.S.C. 154(b) by 419 days.

(21) Appl. No.: 10/354,481

(22) Filed: Jan. 30, 2003

Related U.S. Application Data (60) Provisional application No. 60/354,453, filed on Feb. 4, 2002.

(51) Int. Cl.[7] ............................................. A61B 5/05
(52) U.S. Cl. ................................................... 600/547
(58) Field of Search ............................. 600/547, 587, 600/402, 490, 322, 309, 310; 702/56, 190; 341/155; 436/149; 356/317; 324/77 B (56) References Cited

U.S. PATENT DOCUMENTS

| | | | |
|---|---|---|---|
| 4,093,988 A | 6/1978 | Scott | |
| 4,782,284 A | 11/1988 | Adams et al. | |
| 4,939,469 A | 7/1990 | Ludwig et al. | |
| 4,950,999 A | 8/1990 | Agnello et al. | |
| 5,248,882 A | 9/1993 | Liang | |
| RE34,663 E | * 7/1994 | Seale | 600/587 |
| 5,370,645 A | 12/1994 | Klicek et al. | |
| 5,370,776 A | 12/1994 | Chen | |
| 5,436,447 A | 7/1995 | Shew | |
| 5,454,377 A | 10/1995 | Dzwonczyk et al. | |
| 5,532,936 A | 7/1996 | Perry | |
| 5,565,982 A | 10/1996 | Lee et al. | |
| 5,633,801 A | 5/1997 | Bottman | |
| 5,684,850 A | 11/1997 | Warburton et al. | |
| 5,696,582 A | 12/1997 | Barwald et al. | |
| 5,737,077 A | 4/1998 | Lee et al. | |
| 5,792,668 A | 8/1998 | Fuller et al. | |
| 5,800,348 A | 9/1998 | Kaestle | |
| 5,807,272 A | 9/1998 | Kun et al. | |

(Continued)

OTHER PUBLICATIONS

B. Rigaud et al., "Tissue Characterization by Impedance: A Multifrequency Approach," Physiol. Meas. 15(2A), A13-A20 (1994).

(Continued)

*Primary Examiner*—Max F. Hindenburg
*Assistant Examiner*—Brian Szmal
(74) *Attorney, Agent, or Firm*—Holland & Bonzagni, P.C.; Donald S. Holland, Esq.

(57) ABSTRACT

A spectrometer for measuring the complex impedance spectrum of tissue comprises: a multi-frequency excitation current generator; a demodulation signal generator; two identical amplification/demodulation circuits; an A/D converter; and a microprocessor for signal processing. In use, the current generator excites the tissue sample and a series-connected reference impedance. The voltages generated in the tissue and reference are measured, demodulated, and digitized in parallel using the demodulation signal generator, the two amplification/demodulation circuits, and the A/D converter. Demodulation is done using the same demodulation signal generated at a frequency with a preset difference from the excitation signal, which allows measurements to be made at a low frequency independent of the excitation frequency. The microprocessor then calculates the complex impedance spectrum in relation to the reference signal. Because the measurements are relative, they are independent of both the excitation current amplitude of the phase of the excitation and demodulation signals.

20 Claims, 5 Drawing Sheets

U.S. PATENT DOCUMENTS

| | | |
|---|---|---|
| 5,810,742 A | 9/1998 | Pearlman |
| 5,870,051 A | 2/1999 | Warburton et al. |
| 5,873,054 A | 2/1999 | Warburton et al. |
| 6,055,452 A | 4/2000 | Pearlman |
| 6,160,382 A | 12/2000 | Yoon et al. |
| 6,208,147 B1 | 3/2001 | Yoon et al. |

OTHER PUBLICATIONS

R. Pallas-Areny & J.G. Webster, "Bioelectric Impedance Measurements Using Synchronous Sampling," IEEE Trans. on Biomed. Eng., vol. 40 No. 8, pp. 824-829 (Aug. 1993).

* cited by examiner

FIG. 5 ly, it is a primary object of the present invention
COMPLEX IMPEDANCE SPECTROMETER USING PARALLEL DEMODULATION AND DIGITAL CONVERSION This application claims priority from a Provisional Application, Ser. No. 60/354,453, filed Feb. 4, 2002.

FIELD OF THE INVENTION

The present invention relates to analytical instruments, and, more particularly, to devices for measuring the complex impedance spectrum of tissue or other objects or systems.

BACKGROUND OF THE INVENTION

Complex impedance spectrometry is used in a variety of applications including transmission line and biomedical tissue analysis. Impedance spectrometry measurements are either made in the time domain or the frequency domain. In the time domain, impedance spectrometry is performed by exciting the sample or system to be analyzed with an electric current pulse and measuring the resulting deformed voltage pulse. The complex impedance spectrum can then be calculated by applying a Fast-Fourier Transform or other spectral analysis algorithms to the measured pulse time series. The basic method was described by P. J. Hyde in 1970, and further embodiments were described in U.S. Pat. No. 5,633,801 to Bottman and U.S. Pat. No. 5,454,377 to Dzwonczyket al. This method is limited at high frequencies, however, to the rise time and sampling frequency of the electronics used, and is disadvantageous in that the electronic circuit design becomes difficult for bandwidths larger than 1 MHz.

Impedance spectrometry in the frequency domain involves making measurements at different frequencies, either by sweeping the frequency (as in expensive impedance gain/phase analyzers), or by making discrete measurements at selected frequencies to estimate the impedance spectrum. To simplify the required instrumentation, several methods have been described. For example, one proposed system, as set forth in B. Rigaud et al., "Tissue Characterization by Impedance: A Multifrequency Approach," Physiol. Meas. 15(2A), A13–A20 (1994), involves using parallel amplification and digital conversion circuits to allow for the simultaneous measurement of voltages generated by a variable frequency excitation current source in the sample to be analyzed and in a reference resistance. The captured signals are then processed using a personal computer. Impedance measurements by this system are accurate because the impedance is calculated relative to the reference signal. However, this system requires precise synchronization between the two A/D channels to facilitate accurate phase measurements, and the bandwidth of the system is limited by the sampling frequency of the A/D converters.

For higher bandwidth impedance spectrometry, another proposed system, as set forth in R. Pallas-Areny & J. G. Webster, "Bioelectric Impedance Measurements Using Synchronous Sampling," IEEE Trans. on Biomed. Eng., vol. 40 no. 8, pp. 824–829 (August 1993), utilizes a synchronous demodulation and quadrature sampling method. In this method, the voltage from the excited sample is demodulated to a preset low frequency, independent of the excitation frequency, simplifying the requirements of the sampling and conversion circuit. To retain the phase information, the demodulation and the sampling must be synchronized. The sampling is triggered by a synchronization circuit such that the measurements are made in-phase (0°) and quadrature (90°). This system was further simplified in U.S. Pat. No. 5,807,272 to Kun et al., by using a synchronization circuit accurate at high frequencies and eliminating the need for demodulation. However, synchronization circuits can be expensive and/or difficult to implement, rendering systems that require them less than fully ideal.

Accordingly, it is a primary object of the present invention to provide a high-bandwidth system for accurately measuring the complex impedance spectrum of tissue or other objects, without the need for synchronization circuits or other expensive electronics.

Another primary object of the present invention is to provide a method for high-bandwidth complex impedance spectrometry that is easily and inexpensively implemented using commonly available integrated circuits and microprocessors/personal computers.

Another object of the present invention is to provide a system for measuring complex impedance spectra that simplifies the required hardware, and/or improves the performance of other previously reported methods.

SUMMARY OF THE INVENTION

A high-bandwidth spectrometer for measuring the complex impedance spectrum of tissue or other objects or systems comprises: a multi-frequency excitation current generator; a demodulation signal generator; two identical amplification and demodulation circuits; a two channel A/D converter; and a microprocessor or personal computer for signal processing, recording, and/or display. The current generator is used to excite the system or sample being analyzed, as well as a reference impedance connected in series. The voltages generated in the sample and in the reference impedance are measured, demodulated, and digitized in parallel using the two amplification and demodulation circuits (in conjunction with the demodulation signal generator) and the A/D converter. The signals are demodulated using the same demodulation signal generated at a frequency with a preset difference from the excitation signal. This demodulation allows all measurements to be made at the same low frequency independent of the excitation frequency. By making use of the relatively high sampling frequency of the A/D converter (even the most inexpensive analog-to-digital converters available today have high sampling frequencies), the signals are captured with their relative amplitude and phase information intact, and without the need for any synchronization or timing circuitry. The complex impedance spectrum of the sample is then calculated in relation to the reference signal with software in the microprocessor or personal computer. Because the measurements are relative, they are independent of both the amplitude of the excitation current and the phase of either the excitation or the demodulation signals, and are therefore very accurate.

BRIEF DESCRIPTION OF THE DRAWINGS

These and other features, aspects, and advantages of the present invention will become better understood with respect to the following description, appended claims, and accompanying drawings, in which:

DETAILED DESCRIPTION OF THE INVENTION

Turning now to FIGS. 1–4, a preferred embodiment of a method and system 10 for measuring the complex impedance spectrum of tissue or some other sample 12, according to the present invention, will now be given. The system 10 (also sometimes referred to as a spectrometer) generally comprises: a multi-frequency excitation current generator 14; a demodulation signal generator 16; two identical amplification and demodulation circuits 18, 20; and a signal processor and/or control device 21 (signal processing means) comprising a two channel A/D converter 22 and a microprocessor or personal computer 24 for signal processing, recording, and/or display. The current generator 14 is used to excite the sample 12 being analyzed, as well as a reference impedance 26 electrically connected to the sample 12 in series. The voltage $V_s$ generated in the sample 12 and the voltage $V_r$ generated in the reference impedance 26 are measured, demodulated and digitized in parallel, and the complex impedance spectrum of the sample 12 is then calculated in relation to the reference signal with software in the microprocessor or personal computer 24.

The system 10 described herein is an impedance spectrometer that utilizes demodulation and parallel digital conversion, in conjunction with digital processing (using readily available microprocessors or personal computers), to simplify the instrumentation required for an accurate, high-bandwidth measurement in the frequency domain. In the system 10, since the frequency of the demodulated measured signals (of the sample 12 and reference 26) is constant and can be many orders of magnitude smaller than the sampling frequencies of available A/D converters, any error in phase between the two signals will be constant and negligible so there is no need for any synchronization or timing circuitry between the two channels. Furthermore, since the phase is calculated from the difference in phase between the two demodulated signals, and since the latter is independent of the phase of the unmodulated signals, the demodulation need not be synchronized. Finally, since the amplitude (gain) measurement is relative to the amplitude of the reference signal, the measurements are independent of the excitation current amplitude, and will be very accurate independent of the accuracy and stability of the excitation current generator.

Figure 1:
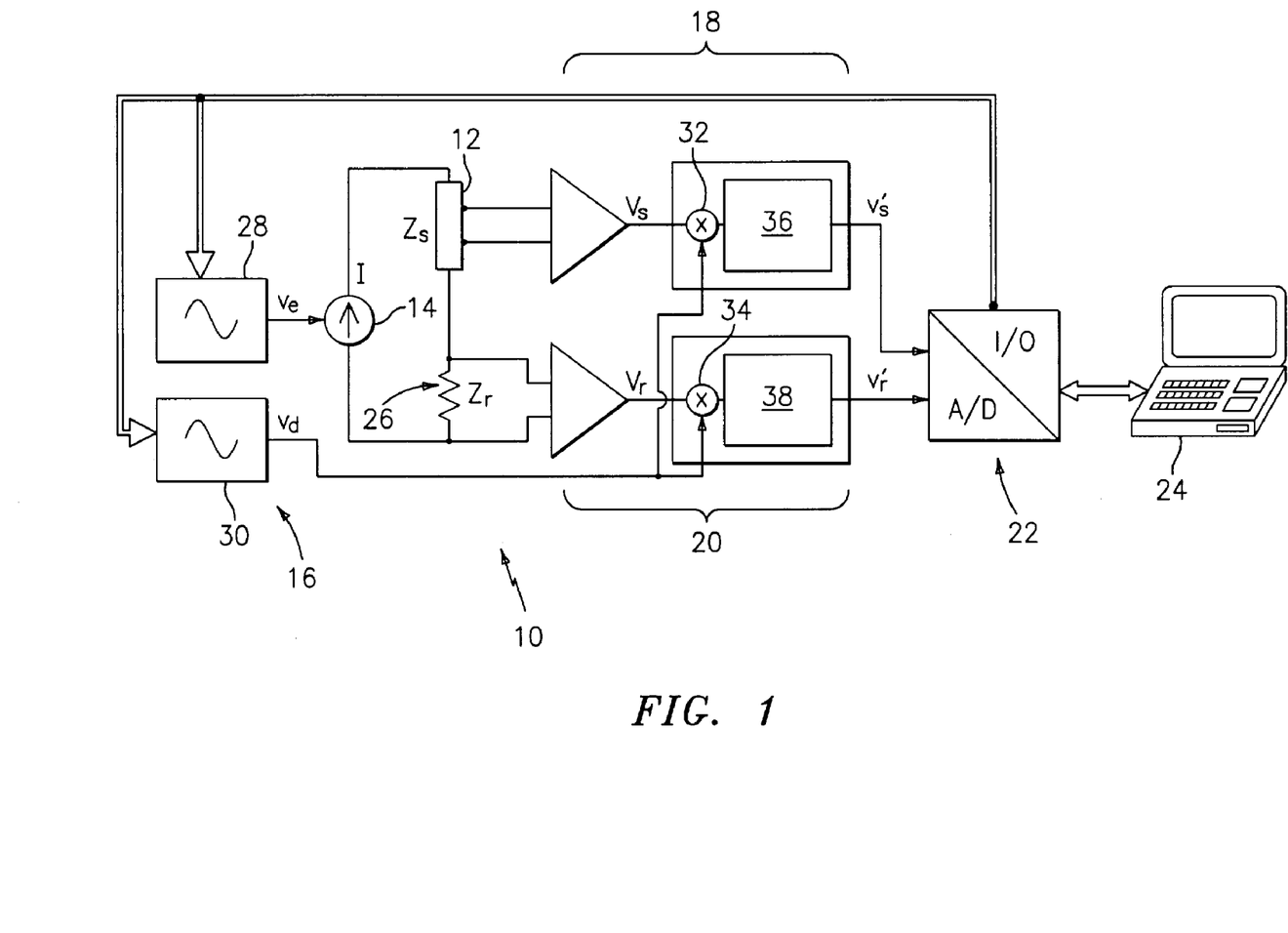
FIG. 1 is a schematic view of a complex impedance spectrometer according to the present invention.

As mentioned above, with reference to FIG. 1, the spectrometer 10 comprises the excitation current generator 14, the demodulation signal generator 16, the two identical amplification and demodulation circuits 18, 20, the two channel A/D converter 22, and the microprocessor or personal computer 24. The excitation signal $v_e$ and demodulation signal $v_d$ are generated using programmable digital synthesizers 28, 30, respectively. These are programmed or controlled by the microprocessor 24 to oscillate sinusoidally at predetermined frequencies $\omega_e$ and $\omega_{dm}$, respectively, producing the signals $$v_e(\omega_e,\ t)=V_e \sin(\omega_e t)$$

and $$v_d(\omega_d,\ t)=V_d \sin(\omega_d t).$$

The frequency difference between the two signals is small (i.e., around 100 Hz or less) and substantially constant (i.e., constant but for inherent system variations such as electrical noise), $$\omega_e-\omega_{dm}=\Delta\omega.$$

Figure 2A:
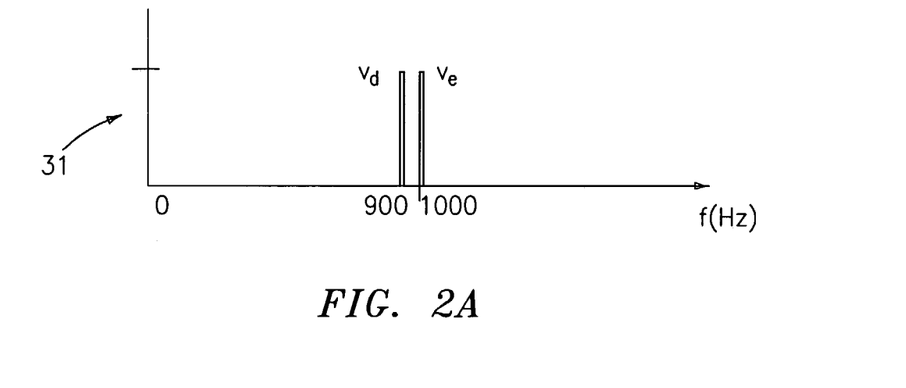
FIG. 2A is a graph showing an excitation signal and a demodulation signal utilized in the spectrometer.

FIG. 2A shows exemplary synthesizer output signals 31, in the form of the excitation and demodulation signals $v_e$ and $v_d$, with the former having a frequency of 1 kHz and the latter a frequency of 900 Hz, for a difference of 100 Hz.

The excitation signal $v_e$ then drives the alternating current source 14 to inject an excitation current $I(\omega_e)$ into the system or sample 12 being analyzed and into the reference resistance 26 connected in series. As should be appreciated, the analyzed sample 12 is electrically connected to the system 10 by any appropriate sample connection mechanism or means, e.g., for an electronic system, by electrical leads, test probes, or some other appropriate connector, and for tissue, by electrodes or the like. The sample 12 has an unknown complex impedance, $$Z_s(\omega)=|Z_s(\omega)|\cos\theta(\omega)+j|Z_s(\omega)|\sin\theta(\omega),$$

where $|Z_s(\omega)|$ is the amplitude spectrum and $\theta(\omega)$ is the phase spectrum. The reference resistance 26 (a resistor or the like) is constant and has a known impedance $$Z_r(\omega)=R.$$

The generated voltage amplitude in the sample 12, $$V_s(\omega_e)=I(\omega_e)Z_s(\omega_e),$$

and in the reference resistance 26, $$V_r(\omega_e)=I(\omega_e)R,$$

are then measured and demodulated in parallel using the same demodulation signal $v_d$ in conjunction with the amplification and demodulation circuits 18, 20. The demodulation is performed using multipliers 32, 34 and bandpass filters 36, 38 centered about the frequency $\Delta\omega$. The multipliers 32, 34 produce the following signals:

$$V_s \sin(\omega_e t+\theta)\cdot V_d \sin(\omega_d t+\theta_d)= V_s V_d \sin((\omega_e-\omega_d)t+\theta-\theta_d)+V_s V_d \sin((\omega_e+\omega_d)t+\theta+\theta_d)$$

and $$V_r \sin(\omega_e t)\cdot V_d \sin(\omega_d t+\theta_d)=V_r V_d \sin((\omega_e-\omega_d)t-\theta_d)+V_r V_d \sin((\omega_e+\omega_d)t+\theta_d).$$

Figure 2B:
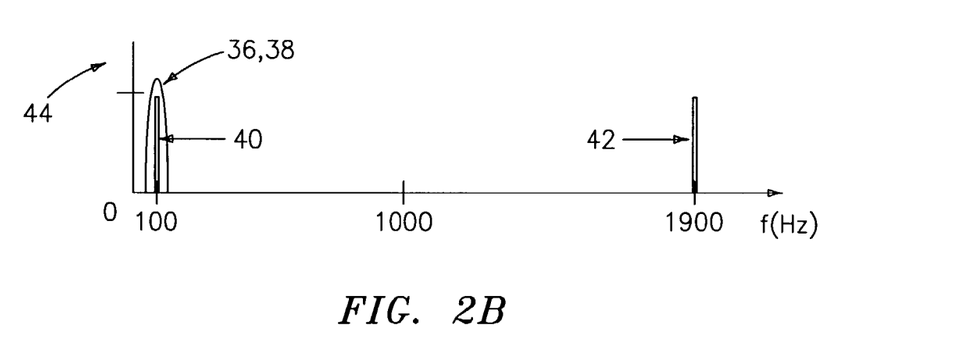
FIG. 2B is a graph showing the output of a signal multiplier portion of the spectrometer.

These are shown graphically in FIG. 2B as a difference band 40 and a sum band 42.

Figure 2C:
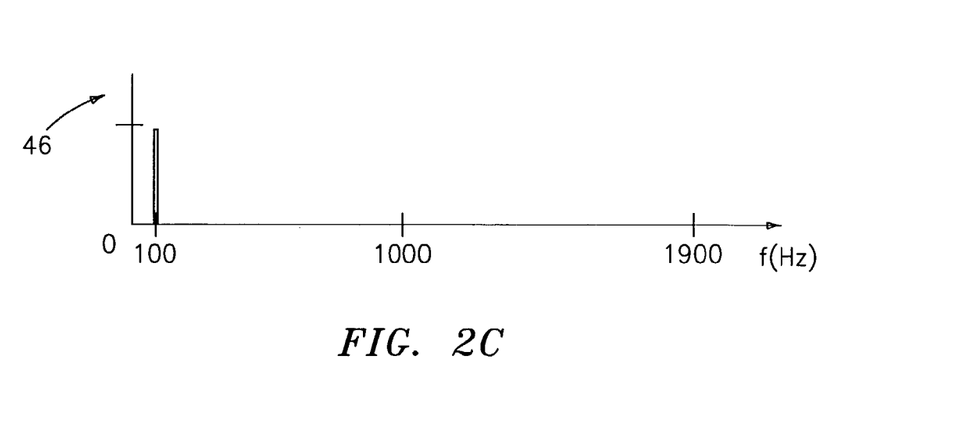
FIG. 2C is a graph showing the output of a filter portion of the spectrometer.

Next, the band pass filters 36, 38 eliminate the higher frequency sinusoid leaving the demodulated signals provenance $$v_s'(t)=V_s V_{dm} \sin(\Delta\omega t+\theta-\theta_d)$$

and $$v_r'(t)=V_r V_{dm} \sin(\Delta\omega t-\theta_d),$$

whose amplitudes are proportional to the amplitudes of the original signals measured at the excitation frequency $\omega_e$, and whose relative phase is equal to the phase shift θ in the sample 12. This process is shown graphically in FIGS. 2B and 2C, with the former showing multiplier output 44 as a function of frequency, and the latter showing filter output 46 as a function of frequency.

Figure 3:
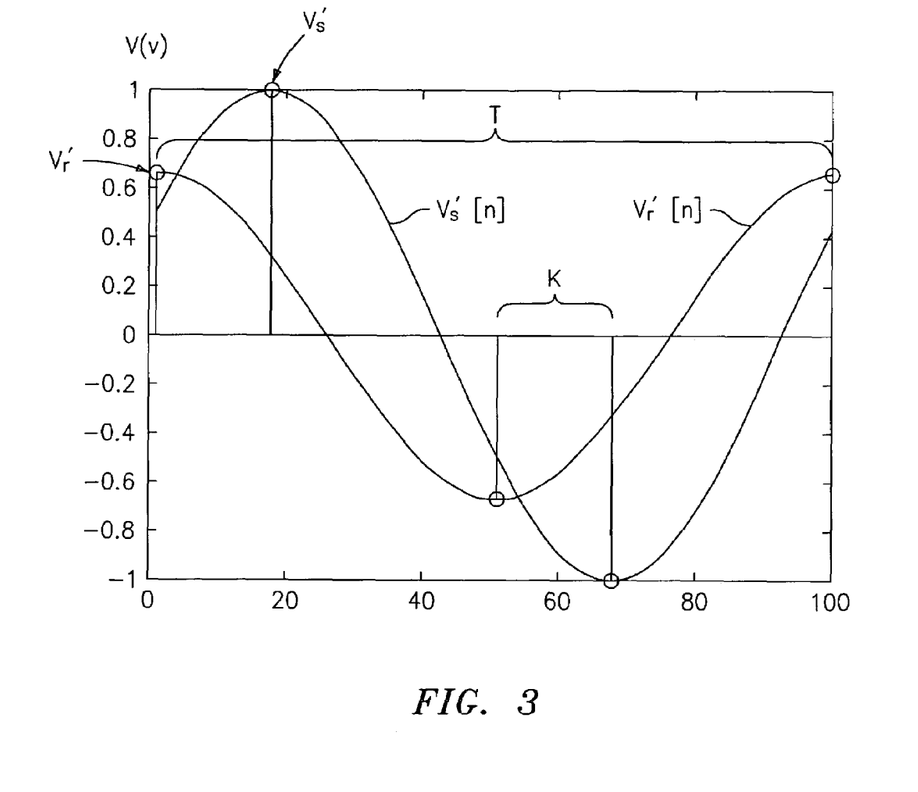
FIG. 3 is a graph showing how the amplitude and phase of the measured impedance are calculated at a particular excitation frequency.
Figure 4:
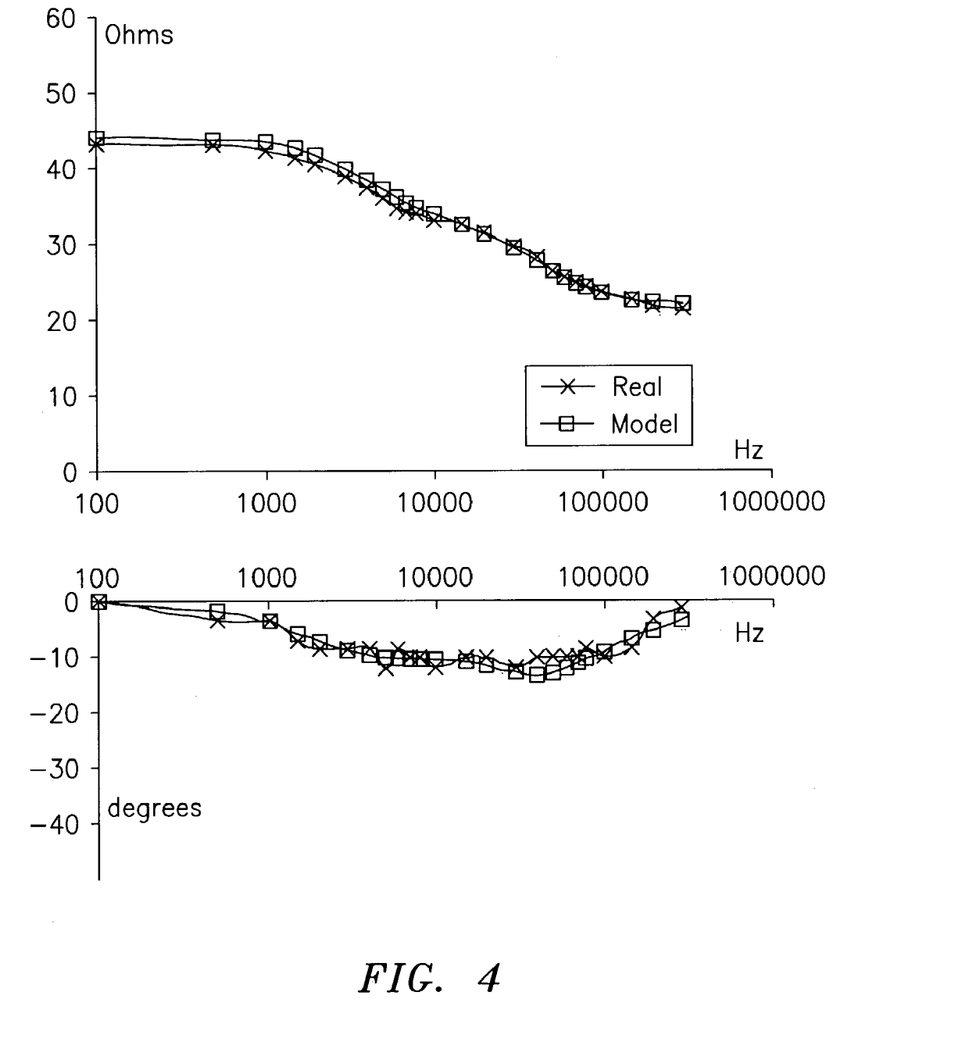
FIG. 4 is a representative graph showing a complex impedance spectra.

Both signals are then simultaneously or alternately digitized and transmitted to the microprocessor 24 by the A/D converter 22. In software, the amplitude and phase at the particular excitation frequency $\omega_e$ are calculated from the acquired signals as follows, as shown graphically in FIG. 3. The amplitude of the impedance in ohms is $$|Z_s(\omega_e)|=R(V_s'/V_r')$$

where $V_s'$ and $V_r'$ are the peak to peak amplitudes of the demodulated and recorded signals of the sample and reference, respectively. The phase in degrees is $$\theta(\omega_e)=K(360°/T)$$

where K is the time shift between $v_s'$ and $v_r'$ and T is the period of both signals. From the amplitude and phase, it is then possible to calculate resistance, reactance, permittivity or any other parameter that might be useful for analysis. By repeating these measurements at different frequencies over the entire bandwidth of interest, the complex spectrum can then be reconstructed, either by interpolation or by solving the Prony equations (see J. P. Morucci et al., "Bioelectrical Impedance Techniques in Medicine", Crit. Rev. in Biomedical Engineering, Vol. 24, Issues 4–6 (1996); see also S. L. Marple, *Digital Spectral Analysis with Applications*, Prentice-Hall, Englewood Cliffs, N.J.), to estimate the spectrum. Spectra can then be displayed graphically, saved in digital form or printed by the computer 24, as illustrated in FIG. 4, which shows an example of impedance amplitude and phase as a function of frequency.

Although the present invention has been illustrated as having a signal processor and/or control device (signal processing means) comprising an A/D converter and computer or microprocessor, it should be appreciated that a stand-alone signal processor (either analog or digital) or some other sort of electronic processing mechanism or circuit (with our without computer, microprocessor, and/or A/D converter portions) could be used instead, without departing from the spirit and scope of the invention.

As should be appreciated, the multi-frequency excitation current generator 14 and synthesizer 28 may be characterized together as an excitation device or means for applying a multi-frequency current to the tissue or other sample 12 and reference 26. Additionally, although these have been illustrated as comprising separate elements, it should be appreciated that the synthesizer and current generator could be provided as an unitary or integrated electrical device or system.

Figure 5:
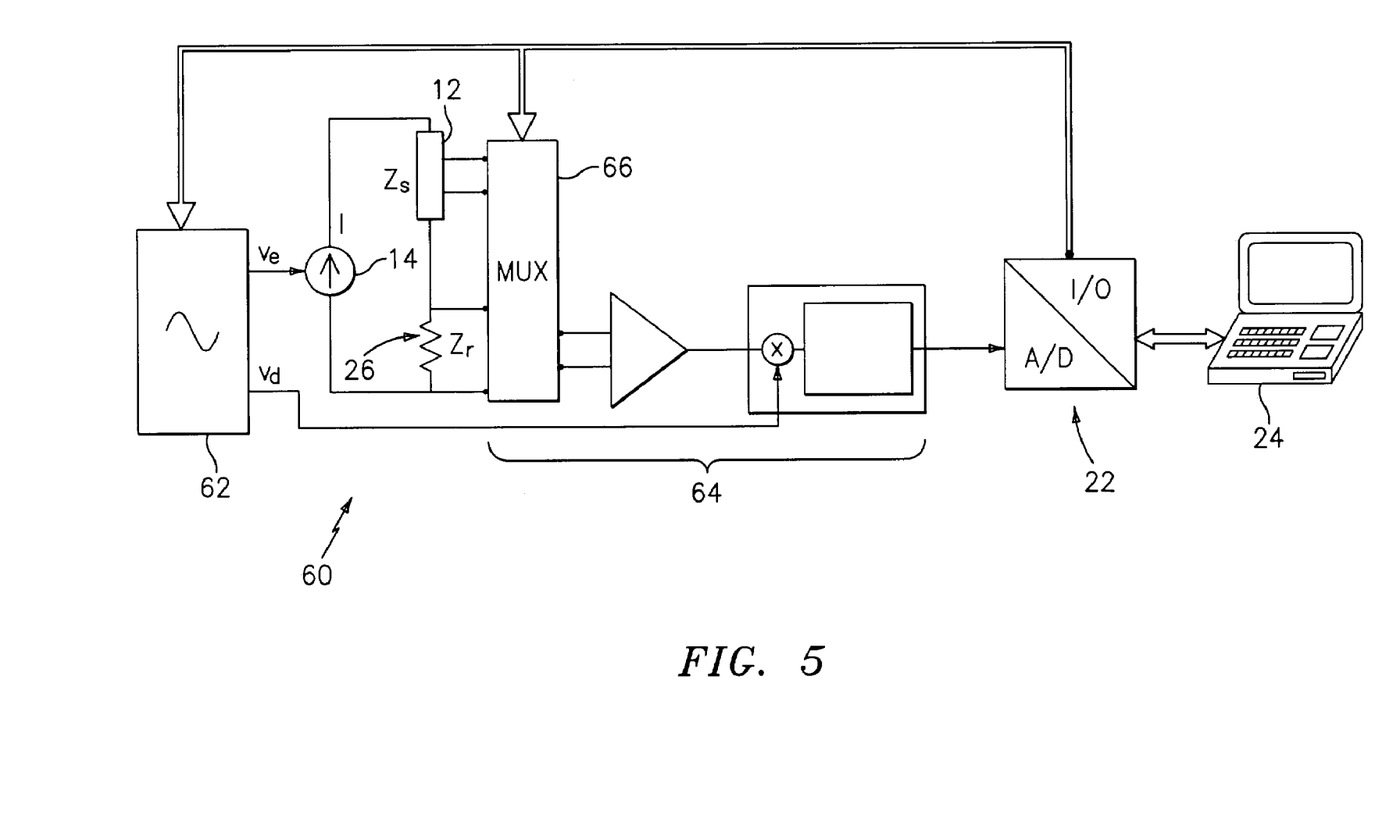
FIG. 5 is a schematic view of an alternative embodiment of the present invention.

FIG. 5 shows a possible alternative embodiment 60 of the present invention. Here, instead of having two synthesizers for generating the excitation and demodulation signals, the spectrometer 60 would have a single, multi-output synthesizer 62 (signal generation means) configured to output the excitation and demodulation signals $v_e$, $v_d$. Additionally, instead of having two amplification/demodulation circuits, the spectrometer 60 would have a single amplification/demodulation circuit 64 including a multiplexer unit 66. The output of the multiplexer 66 would be attached to the input of the amplification/demodulation portion of the circuit 64, while its inputs would be connected to the sample and reference impedance outputs.

In use, the synthesizer 62 would be controlled by the computer 24 and/or programmed to produce the excitation and demodulation signals. The impedance output signals $V_s$, $V_r$ would be routed into the multiplexer 66, which would be controlled by the computer 24 to sequentially output the impedance signals. For example, at each particular excitation frequency, the computer 24 would first cause the multiplexer to pass the sample impedance signal $V_s$, which would be processed by the amplification/demodulation circuit 64 as described above, and then processed/recorded by the computer 24. Subsequently, the computer 24 would cause the multiplexer 66 to pass the reference impedance signal $V_r$ for processing and recording. Of course, the computer 24 would correlate the two separately, sequentially-processed signals in terms of time, period, etc.

Although the system of the present invention has been generally illustrated as comprising a number of separate, interconnected elements and/or circuits, which could be implemented using discreet components, it should be appreciated that the system could be implemented to a large extent as an ASIC, other integrated circuit, or the like without departing from the spirit and scope of the invention.

Since certain changes may be made in the above described complex impedance spectrometer using parallel demodulation and digital conversion, without departing from the spirit and scope of the invention herein involved, it is intended that all of the subject matter of the above description or shown in the accompanying drawings shall be interpreted merely as examples illustrating the inventive concept herein and shall not be construed as limiting the invention.

Having thus described the invention, what is claimed is:

1. A system for measuring the complex impedance spectrum of a sample, said system comprising:
   a. an excitation circuit comprising: a sample connection mechanism; a reference impedance electrically connected in series to the sample connection mechanism; and a multi-frequency excitation device electrically connected in series to the sample connection mechanism and reference impedance;
   b. first and second amplification/demodulation circuits respectively connected in parallel to the sample connection mechanism and reference impedance;
   c. a demodulation signal generator electrically connected to the first and second amplification/demodulation circuits; and
   d. a signal processor electrically connected to the first and second amplification/demodulation circuits.

2. The system of claim 1 wherein:
   a. the first amplification/demodulation circuit comprises: a first amplifier having an input electrically connected in parallel to the sample connection mechanism; a first multiplier electrically connected to an output of the first amplifier and to the demodulation signal generator; and a first bandpass filter electrically connected to the first multiplier and to the signal processor; and
   b. the second amplification/demodulation circuit comprises: a second amplifier having an input electrically connected in parallel to the reference impedance; a second multiplier electrically connected to an output of the second amplifier and to the demodulation signal generator; and a second bandpass filter electrically connected to the second multiplier and to the signal processor.

3. The system of claim 1 wherein:
   a. the excitation device is configured to generate an excitation signal at a first frequency; and
   b. the demodulation signal generator is configured to generate a demodulation signal at a second frequency different from the first frequency, wherein the difference between the first frequency and the second frequency is substantially constant.

4. The system of claim 3 wherein each amplification/demodulation circuit has a bandpass filter set at a third frequency about the same as the difference between the first frequency and the second frequency.

5. The system of claim 3 wherein:
   a. the first amplification/demodulation circuit comprises: a first amplifier having an input electrically connected in parallel to the sample connection mechanism; a first multiplier electrically connected to an output of the first amplifier and to the demodulation signal generator; and a first bandpass filter electrically connected to the first multiplier and to the signal processor and set at a third frequency about the same as the difference between the first frequency and the second frequency; and
   b. the second amplification/demodulation circuit comprises: a second amplifier having an input electrically connected in parallel to the reference impedance; a second multiplier electrically connected to an output of the second amplifier and to the demodulation signal generator; and a second bandpass filter electrically connected to the second multiplier and to the signal processor and set at the third frequency.

6. A system for measuring the complex impedance spectrum of a sample, said system comprising:
   a. an excitation circuit comprising: a sample connection mechanism; a reference impedance electrically connected in series to the sample connection mechanism; and a multi-frequency excitation device electrically connected in series to the sample connection mechanism and reference impedance, said excitation circuit being configured to generate an excitation signal at a first variable frequency;
   b. first and second amplification/demodulation circuits respectively connected in parallel to the sample connection mechanism and reference impedance;
   c. a demodulation signal generator electrically connected to the first and second amplification/demodulation circuits and configured to generate a demodulation signal at a second variable frequency; and
   d. a signal processor electrically connected to the first and second amplification/demodulation circuits; wherein:
   e. the difference between the first variable frequency and the second variable frequency is substantially constant; and
   f. each amplification/demodulation circuit comprises: an amplifier; a multiplier electrically connected to the amplifier and to the demodulation signal generator; and a bandpass filter electrically connected to the multiplier and to the signal processor and set at a third frequency about the same as the difference between the first and second variable frequencies.

7. A system for measuring the complex impedance spectrum of a sample, said system comprising:
   a. a sample, and a reference impedance electrically connected in series to the sample;
   b. at least one signal generator configured to generate an excitation signal at a first variable frequency and a demodulation signal at a second variable frequency different from the first variable frequency, wherein the difference between the first and second variable frequencies is substantially constant, and said signal generator being operably electrically connected to the reference impedance and sample for applying the excitation signal thereto and thereby generating a base reference signal and a base sample signal;
   c. a demodulation circuit operably electrically connected to the sample, reference impedance, and signal generator, said demodulation circuit being configured to output a demodulated reference signal and a demodulated sample signal by: separately multiplying the base reference signal and the base sample signal with the demodulation signal; and separately filtering out portions of the multiplied signals substantially above and below a bandpass frequency equal to the difference between the first and second variable frequencies; and
   d. a signal processor operably electrically connected to the demodulation circuit and configured to calculate the complex impedance spectrum of the sample based on the demodulated reference signal and the demodulated sample signal.

8. The system of claim 7 wherein the signal processor comprises an A/D converter electrically connected to the demodulation circuit and a computer electrically connected to an output portion of the A/D converter.

9. The system of claim 7 wherein the demodulation circuit comprises:
   a. a first demodulation sub-circuit comprising: a first amplifier electrically connected in parallel to the sample and configured to amplify the base sample signal; a first multiplier electrically connected to the first amplifier and to the signal generator and configured to multiply the amplified base sample signal with the demodulation signal; and a first bandpass filter electrically connected to the first multiplier and to the signal processor and centered at the bandpass frequency; and
   b. a second demodulation sub-circuit substantially identical to the first demodulation sub-circuit and comprising: a second amplifier electrically connected in parallel to the reference impedance and configured to amplify the base reference signal; a second multiplier connected to the second amplifier and to the signal generator and configured to multiply the amplified base reference signal with the demodulation signal; and a second bandpass filter electrically connected to the second multiplier and to the signal processor and centered at the bandpass frequency.

10. A system for measuring the complex impedance spectrum of a sample, said system comprising:
    a. a sample, and a reference impedance electrically connected in series to the sample;
    b. at least one signal generator operably electrically connected to the reference impedance and sample and configured to generate a base reference signal and a base sample signal by applying an excitation signal to the reference impedance and to the sample;
    c. a demodulation circuit operably electrically connected to the sample and reference impedance and configured to output a demodulated reference signal and a demodulated sample signal by separately demodulating the base reference signal and the base sample signal; and
    d. a signal processor operably electrically connected to the demodulation circuit and configured to calculate the complex impedance spectrum of the sample based on the demodulated reference signal and the demodulated sample signal.

11. The system of claim 10 wherein the demodulation circuit comprises:
   a. a first demodulation sub-circuit electrically connected in parallel to the sample; and
   b. a second demodulation sub-circuit electrically connected in parallel to the reference impedance and substantially identical to the first demodulation sub-circuit.

12. The system of claim 10 wherein:
   a. the at least one signal generator is configured to generate the excitation signal at a first variable frequency and to generate a demodulation signal at a second variable frequency different from the first variable frequency, wherein the difference between the first variable frequency and the second variable frequency is substantially constant;
   b. the demodulation circuit is operably electrically connected to the signal generator for receiving the demodulation signal; and
   c. the demodulation circuit is configured to separately demodulate the base reference signal and the base sample signal by: separately multiplying the base reference signal and the base sample signal with the demodulation signal; and
   separately filtering out portions of the multiplied signals substantially above and below a bandpass frequency equal to the difference between the first and second variable frequencies.

13. A system for measuring the complex impedance spectrum of a sample, said system comprising:
   a. a sample, and a reference impedance electrically connected in series to the sample;
   b. signal generation means for generating an excitation signal having a first variable frequency and a demodulation signal having a second variable frequency different from the first variable frequency, wherein the difference between the first and second variable frequencies is substantially constant, and said signal generation means being operably electrically connected to the sample and to the reference impedance for applying the excitation signal thereto;
   c. demodulation means, operably electrically connected to the sample, reference impedance, and signal generation means, for demodulating signals produced across the sample and reference impedance by the excitation signal; and
   d. signal processing means, operably electrically connected to the demodulation means, for processing the demodulated signals.

14. A method for measuring the complex impedance spectrum of a sample, said method comprising the steps of:
   a. generating a base reference signal and a base sample signal by applying an excitation signal to a sample and to a reference impedance electrically connected in series to the sample;
   b. generating a demodulated reference signal and a demodulated sample signal by separately demodulating the base reference signal and the base sample signal; and
   c. calculating the complex impedance spectrum of the sample by electronically processing the demodulated reference signal and the demodulated sample signal.

15. The method of claim 14 wherein the step of calculating the complex impedance spectrum of the sample comprises the sub-steps of digitizing the demodulated sample signal and the demodulated reference signal and electronically mathematically calculating the complex impedance spectrum of the sample using the digitized demodulated sample and reference signals.

16. The method of claim 14 wherein:
   a. the excitation signal is at a first variable frequency;
   b. the method further comprises the step of generating a demodulation signal at a second variable frequency different from the first variable frequency, wherein the difference between the first variable frequency and the second variable frequency is substantially constant; and
   c. the base reference signal and the base sample signal are separately demodulated by: separately multiplying the base sample signal and the base reference signal with the demodulation signal; and separately filtering out portions of the multiplied signals substantially above and below a bandpass frequency equal to the difference between the first and second variable frequencies.

17. A method for measuring the complex impedance spectrum of a sample, said method comprising the steps of:
   a. generating a base sample signal and a base reference signal by applying an excitation signal having a first frequency to a sample and to a reference impedance electrically connected in series to the sample;
   b. generating a demodulated sample signal and a demodulated reference signal by: separately multiplying the base sample signal and the base reference signal with a demodulation signal have a second frequency different from the first frequency, wherein the difference between the first and second frequencies is substantially constant; and separately filtering out portions of the multiplied signals substantially above and below a bandpass frequency equal to the difference between the first and second frequencies;
   c. digitizing and electronically storing the demodulated sample signal and the demodulated reference signal;
   d. incrementally changing the first and second frequencies of the excitation and demodulation signals, respectively;
   e. repeating steps a–d across a bandwidth of interest; and
   f. electronically processing the stored demodulated sample and reference signals to calculate the complex impedance spectrum of the sample.

18. The method of claim 17 wherein the base sample signal and base reference signal are voltage signals measured in parallel across the sample and reference impedance, respectively.

19. A method for measuring the complex impedance spectrum of a sample using parallel demodulation and digital conversion, said method comprising the steps of:
   a. generating a base sample signal and a base reference signal by applying an excitation signal to a sample and to a reference impedance electrically connected in series to the sample, said excitation signal having a first frequency;
   b. generating a demodulated reference signal and a demodulated sample signal in parallel by:
      i. multiplying the base sample signal with a demodulation signal having a second frequency different from the first frequency, wherein the difference between the first and second frequencies is substantially constant; and generating an output sample signal by filtering out portions of the multiplied base sample signal and demodulation signal substantially above and below a bandpass frequency equal to the difference between the first and second frequencies; and ii. multiplying the base reference signal with the demodulation signal; and generating an output reference signal by filtering out portions of the multiplied base reference signal and demodulation signal substantially above and below the bandpass frequency;

c. digitally converting and storing the output sample signal and the output reference signal;

d. incrementally changing the first and second frequencies of the excitation and demodulation signals, respectively;

e. repeating steps a–d across a bandwidth of interest; and f. calculating the complex impedance spectrum of the sample by electronically processing the stored, digitally-converted output sample and output reference signals.

20. A method for measuring the complex impedance spectrum of a sample, said method comprising the steps of:

a. applying an excitation signal to a sample and to a reference impedance electrically connected in series to the sample;

b. demodulating a resulting sample signal appearing across the sample;

c. demodulating a resulting reference signal appearing across the reference impedance; and d. electronically processing the demodulated reference signal and the demodulated sample signal.

* * * * *